(12) United States Patent
Chandran

(10) Patent No.: US 6,579,293 B1
(45) Date of Patent: Jun. 17, 2003

(54) INTRAMEDULLARY ROD WITH INTERLOCKING OBLIQUE SCREW FOR TIBIO-CALCANEAL ARTHRODESIS

(76) Inventor: Rama E. Chandran, 4477 W. 118th St., Suite 402, Rolling Hills, CA (US) 90250

( * ) Notice: Subject to any disclaimer, the term of this patent is extended or adjusted under 35 U.S.C. 154(b) by 68 days.

(21) Appl. No.: 09/631,443

(22) Filed: Aug. 2, 2000

(51) Int. Cl.[7] ............................................... A61B 17/56
(52) U.S. Cl. .......................................... 606/64; 606/62
(58) Field of Search ............................. 606/62, 64, 73, 606/98

(56) References Cited

U.S. PATENT DOCUMENTS

| | | | | |
|---|---|---|---|---|
| 4,175,555 A | * | 11/1979 | Herbert | |
| 4,463,753 A | * | 8/1984 | Gustillo | |
| 4,622,959 A | * | 11/1986 | Marcus | |
| 4,644,943 A | * | 2/1987 | Thompson et al. | |
| 4,705,027 A | * | 11/1987 | Klaue | |
| 4,778,468 A | * | 10/1988 | Hunt et al. | |
| 4,976,258 A | * | 12/1990 | Richter et al. | 606/64 |
| 5,549,610 A | * | 8/1996 | Russell et al. | 606/64 |
| 5,653,709 A | * | 8/1997 | Frigg | 606/64 |
| 6,001,101 A | * | 12/1999 | Augagneur et al. | 606/73 |
| 6,168,595 B1 | * | 1/2001 | Durham et al. | 606/64 |
| 6,197,029 B1 | * | 3/2001 | Fujimori et al. | 606/62 |
| 6,270,499 B1 | * | 8/2001 | Leu et al. | 606/64 |

* cited by examiner

Primary Examiner—Ralph A. Lewis
(74) Attorney, Agent, or Firm—Patrick D. Kelly

(57) ABSTRACT

A surgical rod-and-screw kit is disclosed, for use in ankle arthrodesis in patients who suffer from severe bone defects in their ankles. This assembly has a vertical intramedullary rod that is inserted through the bottom of the calcaneum (i.e., the heel bone), and driven upward into the tibia (the shin bone). The assembly also has a threaded pin, referred to herein as an oblique screw, which is positioned at an acute angle with respect to the vertical rod. This oblique screw is inserted through the lower rear surface of the calcaneum, and passes through a slanted hole in the vertical rod. The screw has external threads in the tip region, and this threaded tip enters the lower end of the tibial bone. When this screw is tightened, it compresses the lower end of the tibia bone against the talus and/or calcaneum, which improves the stability of the ankle fixation. This rod-and-screw assembly also reduces the risk and extent of bone damage that can be caused by motion of either or both components during years of use inside a damaged ankle with softened bones. An alignment jig is used during surgery, to help the surgeon align the holes that must be drilled through hard bone for the oblique screw and for fixation screws.

15 Claims, 3 Drawing Sheets

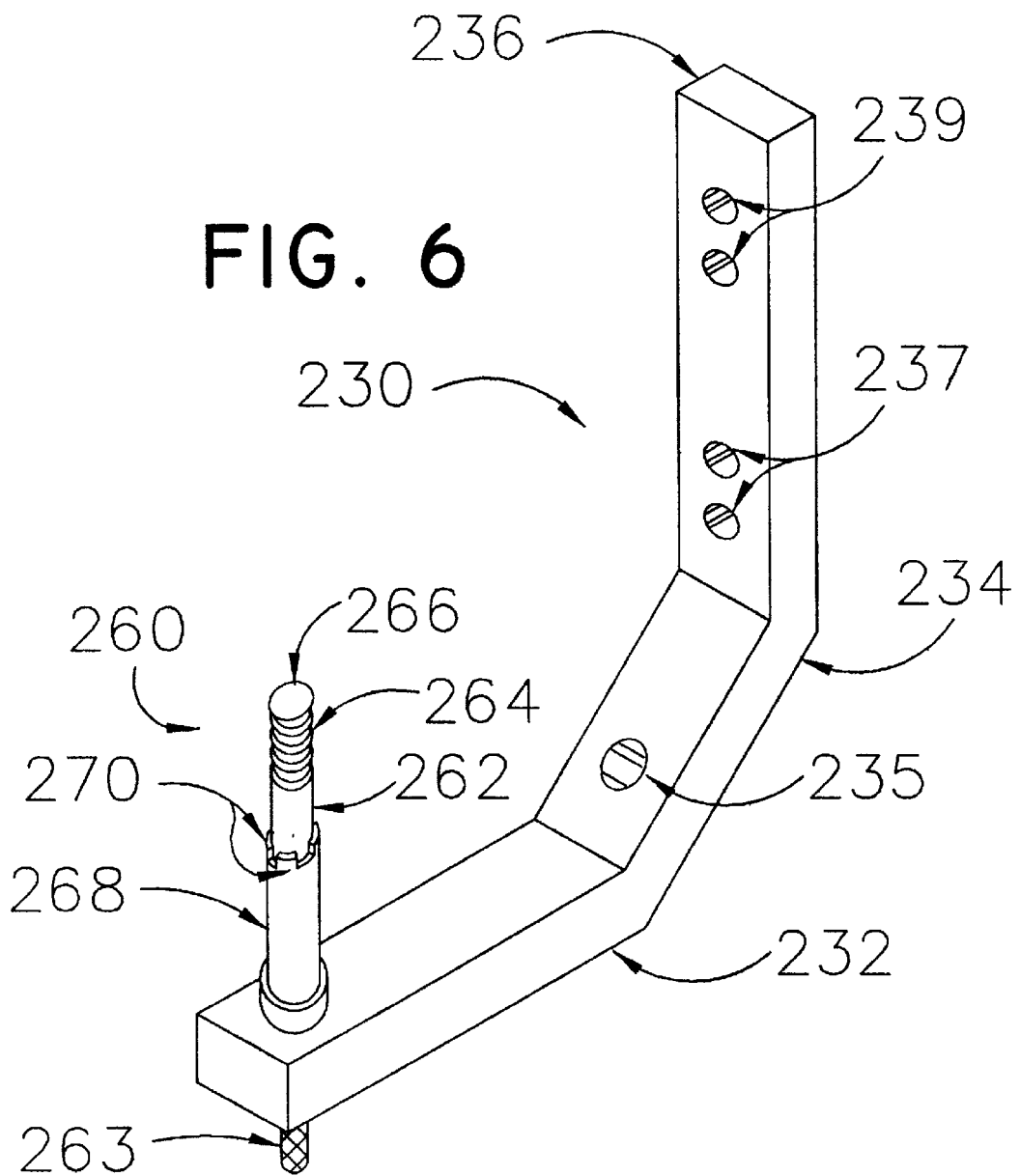

INTRAMEDULLARY ROD WITH INTERLOCKING OBLIQUE SCREW FOR TIBIO-CALCANEAL ARTHRODESIS

BACKGROUND OF THE INVENTION

This invention is in the field of surgical devices, and more particularly relates to rigid fixation devices used to fuse bone structures in badly diseased or deformed ankle joints.

Some patients suffer from various problems which require at least a portion of an ankle joint to be effectively immobilized. This is usually done by inserting one or more rigid rods or pins (typically made of stainless steel and having a diameter roughly the size of a patient's finger) into one or more bones in the ankle, and in the "hindfoot" portion of the foot (i.e., the portion of the foot which includes the heel). This will permanently affix certain bones to other bones. The medical term for this type of permanent bone fixation is "arthrodesis".

As used herein, the terms "rod", "pin", and "nail" are used interchangeably. All three terms refer to a rigid component that is inserted into one or more bones, for the purpose of anchoring, stabilizing, repairing, or supporting the bone(s). Since this invention is limited to devices inserted into an ankle or foot, for the purpose of ankle arthrodesis, any references herein to rod, pin, or screw are limited to devices inserted into a calcaneal and/or tibial bone.

These components are also sometimes referred to as "intramedullary" rods or pins; this term indicates that the rod/pin is inserted into the relatively soft center portion of a bone.

The term "rod" usually implies a relatively large device, while the term "pin" implies a somewhat smaller device; however, there is no clear boundary between these terms.

As used herein, the term "non-threaded" indicates that a rod or pin does not have screw-type threads on its external surface; however, a non-threaded rod or pin can have one or more threaded holes passing through it, for fixation screws, so long as the threads are not exposed on the external surface.

It should also be noted that, while the terms "rod", "pin", or "nail" normally tend to imply that an implant does not have an externally threaded surface, some people and some documents do not adhere to that convention, and some implanted rods, pins, or nails have external threads (including, in some cases, threads that are shallow and are not used to generate thrust or compression as the device is rotated). Accordingly, even though the vertical rods that have been used to date as disclosed herein have not had external threads, such rods can be provided with one or more externally threaded regions if desired, and would still fall within the term "rod" as used herein.

While the type of surgical procedure mentioned above severely limits flexibility and mobility within the ankle joint, it sometimes becomes necessary as a treatment for a condition such as severe arthritis, infection and/or avascular necrosis of one or more bones in the region, congenital deformity of the tibio-talar or talocalcaneal joint, or certain types of neuropathy. In all of those conditions, any motion of the bones relative to each other can cause severe pain in the foot or ankle, to a point where a patient becomes effectively unable to walk or put any pressure on that foot. Accordingly, immobilization of the ankle joint becomes an acceptable price to pay, if the patient can begin to walk again without excruciating pain in the ankle and foot.

Ankle arthrodesis has a long history, and began at least as early as the 1880's (Albert 1882). In the early 1900's, various efforts were made to use long slender bones from corpses (such as the fibula bone), in an attempt to affix various ankle components (e.g., Lexer 1906 and Albee 1915). By the 1960's, intramedullary nailing had advanced to a point of using guide wires to properly locate steel pins, but these approaches tended to suffer from high infection rates. Other authors reported the use of Steinmann pins with external fixation (e.g., Russotti et al 1988), and transfibular pins and cannulated screws (e.g., Pappa et al 1992).

Subsequently, a two-component rod-and-pin structure was developed, with a vertical rod and a horizontal pin that are rigidly affixed to each other, at an angle which is essentially perpendicular, or obtuse (as explained below). This assembly is described and illustrated in articles such as Quill 1999. Since it is the closest known item of relevant prior art, it is also illustrated in FIG. 1, which is a lateral view of the inside surface of a right foot.

The vertical rod is inserted into a hole that is drilled into the bottom of the calcaneum (also called the heel bone, the calcaneal bone, and the os calcis). In patients having a normal or near-normal bone structure, this rod then passes through the talus (also called the talar bone; also called the ankle bone, by laymen), which sits directly on top of the calcaneum, as shown in FIG. 1. Regardless, the vertical rod of the two-pin assembly is driven into the center (marrow) portion of the tibia (the long bone which passes from the knee to the ankle; also called the shinbone by laymen). This vertical rod thereby permanently fuses the calcaneum (heel bone) to the tibia, and immobilizes that portion of the ankle joint. If this type of vertical pin is used by itself, this type of fixation would be called "tibio-calcaneal arthrodesis".

In the second stage of the surgical operation used to emplace the two-pin device of the prior art, the smaller pin is inserted, in a roughly horizontal manner, through a hole drilled into the posterior (rear) face of the calcaneum. It passes through a hole in the vertical rod, and is driven close to the anterior tip of the calcaneal bone. Even though this pin is not strictly horizontal, it is referred to herein as the horizontal pin, to clearly distinguish it from the vertical rod, which is significantly larger and which is emplaced first.

As shown in pictures such as FIG. 1D in Quill 1999 (and in FIG. 1 herein), the anterior tip (i.e., the end that is closer to the patient's toes) of the horizontal pin is slightly lower than the posterior tip (i.e., the end closest to the patient's heel). This establishes an obtuse angle between the rod and the pin, designated as angle αPA in FIG. 1. The roughly horizontal pin (assuming the patient's foot is standing on a horizontal surface) is referred to herein as having a slightly "downward" angle, since the pin is driven forward into the foot from the entry point at the heel.

After both the rod and the pin have been properly emplaced in the patient's foot, they are permanently affixed to the tibial and calcaneal bones, using threaded screws.

Two issues involving bone structures and terminology should be clarified. First, in a normal ankle joint, because of the placement of the bones, a straight rod which passes vertically through the calcaneum (the heel bone) and into the tibia (in the shin) will normally pass through the talus (the ankle bone). Accordingly, a reference to "tibio-calcaneal arthrodesis" usually suggests and implies "tibio-talo-calcaneal" arthrodesis. However, in many patients with severe ankle problems, the talus is extensively degraded, and the posterior portion (on which the tibial weight rests, when a person is standing or walking) may be entirely missing, or shrunken to a point where it is not penetrated by a vertical rod. Indeed, a patient with a complete and intact talus rarely offers a good candidate for tibio-calcaneal arthrodesis. Nevertheless, some patients with talus bones that would be penetrated by a vertical rod may be helped by the invention disclosed herein, as can be determined on a case-by-case basis by a skilled surgeon. Accordingly, the term "tibio-calcaneal" arthrodesis is used herein, regardless of the presence or condition of the talus bone in any specific patient, and regardless of whether the vertical rod component will or will not pass through a talus bone in any specific patient.

The second point of terminology involves the phrase, "tarsal arthrodesis". As is well-known to physicians, the bones in an ankle and foot are divided into three major regions, referred to as the tarsal region (which includes the talus and calcaneal bones, as well as the navicular, cuboid, and certain other bones), the metatarsal region (which includes five relatively long and essentially parallel bones that form the hidden bases of the five toes), and the phalanges (which includes the bones in the toes). Accordingly, a surgical operation that affixes one or more bones in the tarsal portion of the foot can be referred to as tarsal arthrodesis.

All of the rod-and-pin structures that have been developed for ankle arthrodesis over the past 20 years suffer from various limitations. In particular, some patients who have had the device of the prior art inserted into their ankles have suffered from problems involving relative motion between the supposedly affixed tibial and calcaneal bones. This can lead to substantial pain in the affixed joint, and to instability when the patient is walking or standing. It can also lead to additional damage inside the joint, as the screws or other components rub and grind against one or more bones, which are often weakened and relatively soft in patients with severe joint or bone problems.

Accordingly, one object of this invention is to provide an improved type of ankle arthrodesis assembly, which provides better and more stable and reliable fixation of the ankle and hindfoot in patients who need such treatment due to injury or disease of the foot or ankle.

Another object of this invention is to disclose an improved type of ankle arthrodesis assembly for ankle fixation, having a vertical rod which will be inserted vertically through the calcaneal bone and into the lower end of the tibial bone, and an "oblique screw" which will be inserted at a slanted angle, extending upwardly through the calcaneal bone so that a threaded tip enters the lower end of the tibia.

Another object of this invention is to disclose an improved type of ankle arthrodesis assembly for ankle fixation, having an "oblique screw" with a threaded tip that will pass through a smooth slanted hole in a vertical rod and enter the lower end of the tibia bone, thereby allowing the threaded screw to exert compression of the tibia against the calcaneum when the screw is tightened.

Another object of this invention is to disclose that when a surgical implant having rod and screw components, positioned at an acute angle with respect to each other, is properly implanted into an ankle that requires arthrodesis, the acute-angled structure provides greater stability and better performance following surgical implantation.

These and other objects of the invention will become more apparent through the following summary, drawings, and description of the preferred embodiments.

SUMMARY OF THE INVENTION

A surgical rod-and-screw kit is disclosed, for use in ankle arthrodesis in patients who suffer from severe bone defects in their ankles. This assembly has a vertical intramedullary rod that is inserted through the bottom of the calcaneum (i.e., the heel bone), and driven upward into the tibia (the shin bone). The assembly also has a threaded pin, referred to herein as an oblique screw, which is positioned at an acute angle with respect to the vertical rod. This oblique screw is inserted through the lower rear surface of the calcaneum, and passes through a slanted hole in the vertical rod. The screw has external threads in the tip region, and this threaded tip enters the lower end of the tibial bone. When this screw is tightened, it compresses the lower end of the tibia bone against the talus and/or calcaneum, which improves the stability of the ankle fixation. This rod-and-screw assembly also reduces the risk and extent of bone damage that can be caused by motion of either or both components during years of use inside a damaged ankle with softened bones. An alignment jig is used during surgery, to help the surgeon align the holes that must be drilled through hard bone for the oblique screw and for fixation screws.

BRIEF DESCRIPTION OF THE DRAWINGS

FIG. 6 depicts a "jig" structure that will help a surgeon align several holes that must be drilled through bone surfaces with corresponding holes through the vertical rod.

DESCRIPTION OF THE PREFERRED EMBODIMENTS

Figure 1:
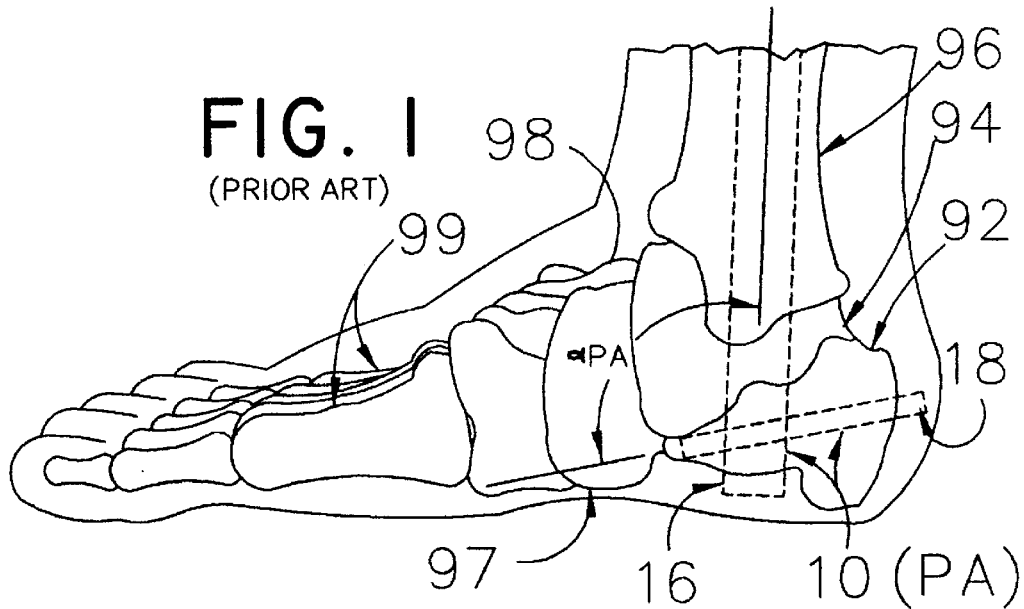
FIG. 1 is a lateral view of the bones inside a foot, depicting an item of prior art having a vertical rod and a roughly horizontal pin with a slight "downward" slope.

Referring to the drawings, FIG. 1 depicts the closest known item of prior art, shown as callout number 10(PA). This drawing is a simplified depiction of what would be seen in an X-ray taken from a lateral (medial) position (i.e., showing the patient's foot 12 from the interior side). All directional terms (such as vertical and horizontal) are used relative to a patient standing on a horizontal floor.

FIG. 1 depicts the bone structure in a normal and healthy foot. These bones include calcaneal bone 92, talus bone 94, and tibial bone 96. FIG. 1 also depicts navicular bone 97, cuboid bone 98, and various metatarsal bones 99, all of which are closer to the anterior (toes) of the foot.

The prior art assembly 10(PA) comprises a vertical rod 16 and a roughly horizontal pin 18. As illustrated in articles such as Quill 1999, horizontal pin 14 slants downward slightly, from its posterior entry point to its anterior tip, when properly emplaced inside a foot. This establishes a slightly obtuse angle between vertical rod 12 and horizontal pin 14, shown as angle $\alpha PA$ in FIG. 1 (where PA refers to "prior art").

FIG. 1 shows the lower end of vertical rod 16 protruding down below the lower surface of the calcaneal bone. This is only for illustration purposes; in actual practice, the lower end of the rod normally will be placed flush with, or inset slightly into, the lower bone surface.

Figure 2:
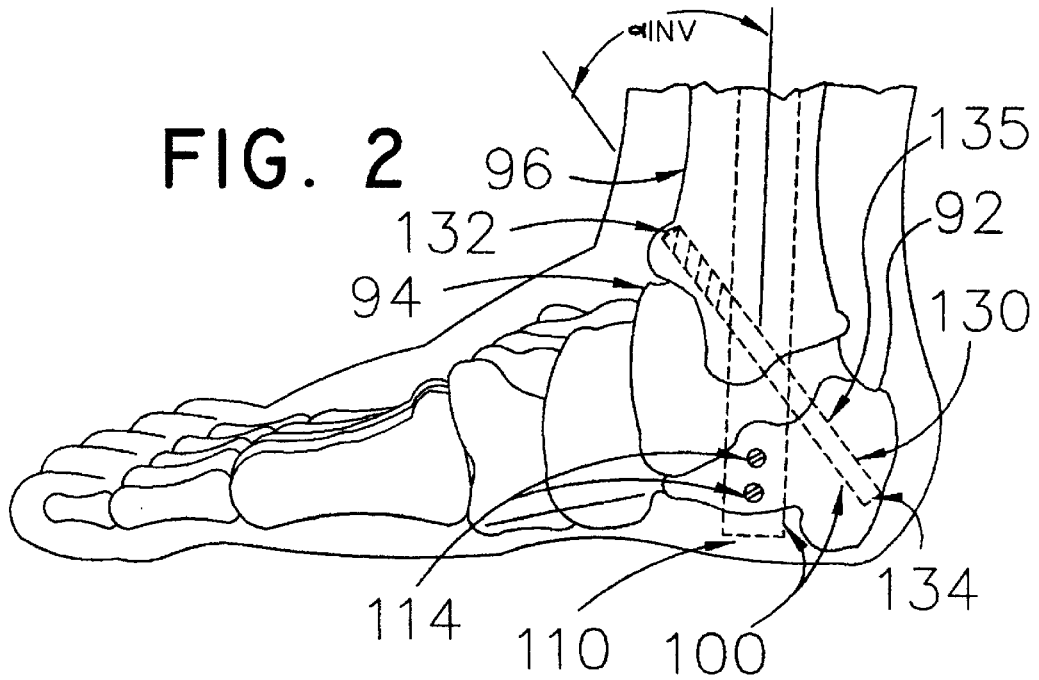
FIG. 2 is a side view of the rod-and-screw assembly of this invention, showing vertical rod and oblique screw inside the major bones of an ankle joint. In this drawing, the posterior portion of the talus bone has been degraded, and no longer separates the tibia from the calcaneum.

In contrast to the prior art shown in FIG. 1, the structure and placement of the surgical assembly of the current invention is shown in FIG. 2. In this drawing, assembly 100 comprises a vertical rod 110 and an oblique screw 130, depicted in a lateral view inside foot 90. This lateral view depicts calcaneal bone 92, talus bone 94, and tibial bone 96.

It should be noted that in FIG. 2, the posterior portion of talus bone 94 has been eroded and degraded, by the weight and repetitive grinding motion of the tibia bone 96 while the patient is walking, to a point where the talus 94 no longer separates the tibia 96 from the calcaneum 92.

Vertical rod 110 has a tip 112, a shaft 113, and a base 124, with various holes and slots described below. During a surgical operation to insert rod-and-screw assembly 100 into a damaged, diseased, or otherwise defective ankle joint, the tip 112 will be pushed through a hole that has been drilled through the bottom of calcaneal bone 92, in the heel.

This preferably should be done with the aid of a "jig" 230 (also called a guide, template, etc.), discussed below and illustrated in FIG. 6. Briefly, during the implantation procedure, vertical rod 110 is screwed to the end of a coupling bolt 260, which is part of alignment jig 230. Jig 230 remains outside the patient's foot, and it can be loosened, rotated 90 degrees at a time, and locked down again. This allows it to provide alignment holes which will help the surgeon accurately position and align several holes (two holes for tibial fixation screws, one hole for the oblique screw, and two more holes for calcaneal fixation screws). These holes, which must be drilled through hard bone, must be closely aligned with corresponding holes in the vertical rod 110, after the vertical rod has been fully inserted into the patient's foot and leg. The design of jig 230, and a preferred method of using it during surgery, are discussed in more detail below.

Figure 3:
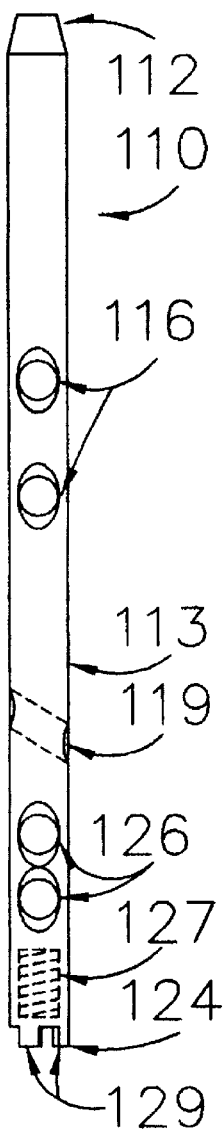
FIG. 3 is a side view of the vertical rod, having a slanted hole which accommodates the oblique screw.

Vertical rod 110 may or may not pass through a portion of talus bone 94, depending on the size and placement of the talus, which can vary substantially in badly damaged or diseased joint. The upper end 112 of vertical rod 110 is driven into the lower end of tibial bone 96. The upper portion of rod 110 should be securely and permanently affixed in the tibial bone, by means such as cementing and/or fixation screws 114 (shown in FIG. 5). Fixation screws 114 can be threaded, to interact with one or more accommodating threaded holes 116 in the shaft of rod 110, as shown in FIG. 3. In most cases, final fixation of vertical rod 110 and oblique screw 130 should not be carried out until after both components have been fully inserted, since the oblique screw 130 must pass through an accommodating slanted hole 119 in vertical rod 110. In the rods used to date, slanted hole 119 has had a smooth internal surface; however, if desired, a slanted hole can be used with a threaded internal surface which will engage threads on the shaft of oblique screw 130.

Vertical rod 110 should be provided with at least one and preferably two lower threaded holes 126, to accommodate fixation screws 128, which will pass through calcaneal bone 92 after placement in a foot. In general, lateral (side-to-side) orientation of at least the lower fixation screws is preferred, so that multiple closely-space coplanar holes (which might weaken the shaft of the vertical rod 110) are avoided.

As discussed below, base 124 of rod 110 is a hollow sleeve. This sleeve is provided with internal threads 127, which accommodate the threaded end of a coupling bolt 260 that is mounted on an alignment jig 230 (discussed below, and illustrated in FIG. 6). Rod base 124 is also provided with four slots 129 in a "cruciate" (orthogonal) arrangement, shown in FIGS. 3 and 5. These slots 129 will accommodate alignment fins 270, which are positioned at the top of a sleeve component 268, which is part of coupling bolt 260. When slots 129 interact with alignment fins 270 on the jig coupling bolt, it allows the alignment jig 230 to be rotated around an axis established by the vertical rod 110, after the rod has been inserted into the tibial bone). The jig can also be "locked down" in controlled 90 degree increments. This allows jig 230 to help the surgeon properly align the holes that must be drilled through the bones in the patient's heel and shin.

After vertical rod 110 has been properly placed, a second hole is drilled into the lower posterior region of the calcaneal bone 92. This hole (which, in a preferred embodiment, has a smooth nonthreaded internal surface) will accommodate oblique screw 130. Oblique screw 130 has tip 132 and base 134, at opposed ends of shaft 135. Tip 132 will be pushed into the hole that has been drilled through the posterior surface of calcaneum 92, and will then be pushed through slanted hole 119 in vertical rod 110.

As used herein, the term "oblique" indicates that screw 130 is positioned at a slanted angle with respect to the main axis of rod 110. This angle, shown in FIG. 1 as αINV (the angle of this invention, as distinct from αPA, the angle of the prior art shown in FIG. 1) will be an acute angle, when measured between the tips of the vertical rod 110 and the oblique screw 130.

For most patients, the preferred angle between rod 110 and screw 130 will usually fall within a range of about 30 to about 50 degrees. Assemblies with an angle of 45 degrees between the rod and screw have been used in several patients, with very good results. However, some patients with severe ankle defects do not have sufficient tibial bone to provide a solid "purchase" (secure grabbing) of the tibia bone, if the oblique screw is positioned at an angle of 45 degrees. Accordingly, assemblies with a 30 degree angle between the rod and screw were used on some patients, with apparently good results, in cases where a 30 degree angle provided stronger and more secure coupling to the tibia bone. Accordingly, vertical rods can be provided with oblique holes at various angles, ranging from about 30 to about 50 degrees, and a surgeon can choose a vertical rod having an optimal angle for a particular patient.

Preferred dimensions for the rod and screw will vary, so that a range of devices having different sizes can be available for patients of different sizes. This will allow a surgeon to select and use two specific components that will work best in that specific patient, after the surgeon has analyzed the nature and severity of the damage, disease, or defect that requires surgical intervention. In one preferred approach, an assortment of vertical rods having lengths of 15, 20, and 25 cm can be provided, with diameters in the range of about 9 to about 14 mm. Similarly, in a preferred approach, oblique screws with lengths of about 5.5 to about 7 cm, and diameters of about 4 to about 7 mm, can be provided. These will allow surgeons to choose rod and screw combinations that will accommodate the majority of patients. If different sizes or angles are needed, they can be stocked by a manufacturer, or fabricated on a custom basis, preferably using computer controlled machining methods (such as laser cutting) to minimize the additional expenses of custom fabrication.

The rod and screw preferably should have beveled but not sharply-pointed tips. As noted above, screw tip 132 should be provided with external threads, in at least a region which extends back about 1.5 cm or more from the tip. These threads should having a spacing and height which allow the threaded tip 132 to securely engage, and pull against, the lower end of the tibial bone, as screw 130 is tightened during surgical placement. Preferred dimensions (including the pitch, depth, and shape of the peaks) have been established for threaded screws that will be inserted into bones; those dimensional are well-known to companies that manufacture such surgical implants. Very fine threads are not used, since they can break and crumble bone material; instead, thread spacings of roughly 1.5 mm (or larger) and a thread height (depth) of more than 1 mm are generally used.

The oblique screw of this invention is referred to as having a "threaded tip region". This phrase does not require that the threads must cover the actual tip of the screw (such as used in screws designed for penetrating wood, sheet metal, etc). Instead, the threaded region merely needs to cover a sufficiently large area slightly behind the tip allow the threads to securely engage the lower end of a tibia bone. If desired, threads can cover all or most of the entire surface of the oblique screw, even if the threaded regions at the tip and the base have different pitches, as discussed below.

The threads on the tip region will allow the screw to pull the tibia bone in a downward direction, as the screw is turned during the final stage of the setting operation. This will help establish compression between the tibia and the calcaneum, in a manner which causes the fixation of the two bones to be more secure and less subject to problems as the foot is used for walking over a span of years or decades.

In conventional ankle arthrodesis, the vertical rod typically does not have an enlarged plate or head at its lower end, and the rod is positioned so that its lower end is either flush with the calcaneal bone, or is sunken slightly into the bone surface. That same approach has been used to date by the Applicant, with apparently good results. If desired, vertical rods with enlarged and/or flattened heads at their lower ends can be tested, either in general or for patients having specific types of ankle problems.

By contrast, the oblique screw requires means for twisting the screw after the tip enters the tibial bone. This has been provided by using an enlarged head 138 (illustrated in FIG. 5) which is "countersunk" into a corresponding enlarged shallow portion of the hole that is drilled or reamed in the calcaneal bone surface. Screw head 138 can be provided with any suitable means for rotation, such as a hexagonal socket-type inset 139, illustrated in FIG. 5, which will accommodate a hexagonal wrench, commonly called an "Allen" wrench.

Figure 4:
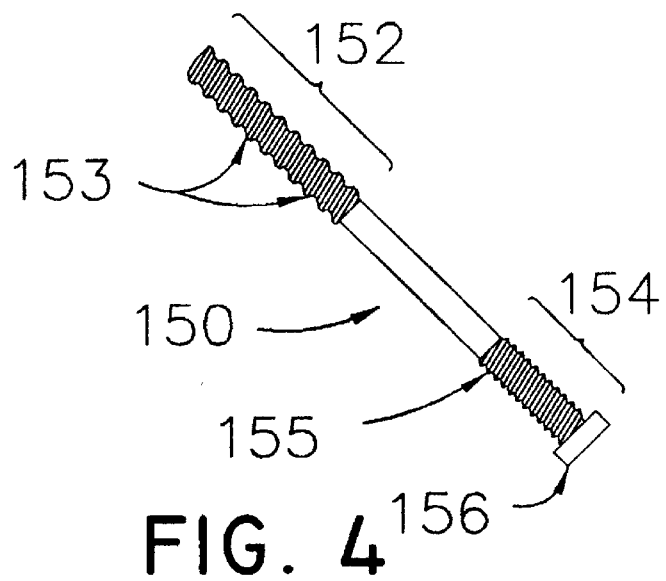
FIG. 4 is a side view of an oblique screw having a threaded tip that will enter a tibial bone, and a base having optional additional threads with a slightly different pitch which will become set in the calcaneal bone.

If desired, an oblique screw can be used with two different threaded regions, as shown in FIG. 4. In this drawing, screw 150 has a threaded tip region 152 with threads 153 that will engage the lower end of a tibial bone, as discussed above, as well as a threaded base region 154 with threads 155 that will engage the calcaneal bone.

In one preferred embodiment, tibial (tip) threads 153 have a first pitch setting (such as, for example, 6 threads per inch) while calcaneal (base) threads 155 have a different pitch setting (such as, for example, 8 threads per inch) which is somewhat more densely spaced. If this design is used, because of the effects of the different pitches on the two threaded surfaces, rotation of the screw will cause the lower end of the tibial bone to be pulled farther toward (and therefore compressed harder against) the upper surface of the calcaneal bone, as threads 195 tighten within the calcaneal bone.

In patients tested to date, the threaded end of the oblique screw "grabs" the tibial bone with sufficient strength to prevent it from rotating in a direction which would loosen the screw (this is often referred to as "backing out). If long-term results indicate that additional preventive measures need to be taken in one or more classes of patients, suitable means (such as cementing, one or more fixation screws or pins, a "key" that can be inserted into a slot in the screw shaft in the region of the exposed calcaneal bone, etc.) can be developed to prevent any possibility of rotation.

The rod, the oblique screw, and any fixation screws should be made of a suitably hard biocompatible material, such as a stainless steel or titanium steel alloy. Such alloys, and methods of fabricating metallic devices as disclosed herein, are conventional and well-known in the art of surgical implants. The surgical procedures that can be used to implant and permanently anchor such devices to bone structures are also well-known to orthopedic surgeons.

Surgical Kits

A final and complete rod-and-screw assembly as disclosed herein will be created, inside an ankle joint, by a surgeon, using components that are contained in a "kit" that can be manufactured and sold by a manufacturing company which specializes in medical devices and surgical implants.

In general, two classes of kits are anticipated. The first type of kit can contain a single set of components (i.e., one vertical rod and one oblique screw), and can also include any additional components that will be needed during the operation, such as fixation screws. Such a kit can be ordered by a surgeon, with the exact sizes of both main components fully specified, after the surgeon has analyzed the problems and needs of a specific patient.

The second type of kit (which might be preferred by a hospital or orthopedic clinic where several surgeons work) can contain a variety of rods and screws, such as a plurality of rods of each desired length (such as 15, 20, and 25 cm) and a plurality of screws of each desired length (such as 5.5 to 7 cm). This will allow a surgeon to select a preferred combination for any specific patient, from among the assortment that is already available at that clinic or hospital.

In general, surgical kits typically enclose any and all implantable components within sealed enclosures that maintain sterility. However, it should be noted that any implanted components disclosed herein can be easily sterilized immediately before use, by autoclaving or similar means.

Figure 5:
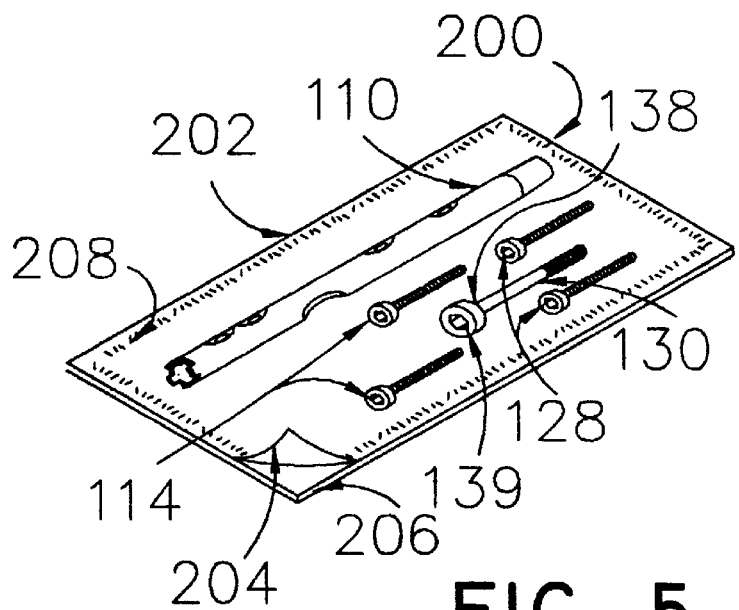
FIG. 5 is a perspective view of an implant kit, with a vertical rod and an oblique screw contained within a sealed package that maintains sterility of both implant components.

FIG. 5 depicts a surgical kit 200, comprising a sealed envelope 202 which contains a vertical rod 110, an oblique screw 130, and several fixation screws 114 and 128. Envelope 202 is made of a front layer 204 (which preferably should be clear, so the contents will be easily visible) and a back layer 206, both made of a suitable material such as plastic. The layers can be sealed to each other by means of a peripheral seal 208, to establish a watertight and airtight enclosure that maintains sterility of the components inside the sealed envelope 202.

It should also be noted that, in the U.S. and most other industrial countries, kits containing surgical implants or other medical devices are normally required by law to be sold with certain types of labelling information, indicating that the device is a medical device and providing various instructions concerning its proper use for medical purposes. Indeed, under the laws administered in the U.S. by the Food and Drug Administration (FDA), a medical device and its package (with labelling information or enclosures) must be treated as a single item of commerce, and it is illegal to sell the item by itself, without the required labelling accompanying the item.

Accordingly, this invention claims a screw with certain traits, as outlined above, which "is packaged in a manner suited for a surgical implant and labelled in a manner which indicates that it is a medical device intended for ankle arthrodesis."

External Alignment Jig and Procedures

FIG. 6 illustrates a "jig" 230, which is briefly mentioned above, and which can also be called a template, guide, etc. This device is used during the surgical procedure, to help ensure proper alignment of the various holes and screws. In the embodiment shown in FIG. 6, jig 230 comprises a horizontal base 232, an oblique arm 234, and a vertical arm 236. As noted above, the terms "horizontal" and "vertical" are used in a fixed manner, assuming that a patient's foot is standing on a horizontal surface, even though that will not be the case during the surgical operation itself.

Jig 230 also comprises a rod coupling bolt 260 (referred to as a "rod coupling component" 260, in the claims). Rod coupling bolt 260 can be detachable from the jig base 232, if desired; this will allow simpler fabrication, and improved sterilization between uses. Unlike a rod and screw set, which will be implanted only once into a single patient, jig 260 is designed for multiple uses in any number of operations.

Oblique arm 234 has hole 235 passing through it, so that a drill bit which passes through hole 235 and penetrates a calcaneal bone, during surgery, will be properly aligned with the oblique hole 119 through rod 110.

The design shown in FIG. 6, which provides a distinct angled portion 234 between base 232 and arm 236, is preferred, since it helps the surgeon (and/or an assistant) exert a desired type of pressure on the patient's heel while a hole is being drilled for the oblique screw, as discussed below. However, oblique arm 234 is not essential; if desired, vertical arm 236 could be connected directly to horizontal base 232, if desired, or the jig could be provided with a rounded curve between base 232 and arm 234. Similarly, it is not essential that arm 236 must be perpendicular to base 232; for example, if oblique arm 234 is omitted, arm 236 might be placed at an obtuse angle with respect to base 232.

Vertical arm 236 has two lower holes 237 and two upper holes 239 passing through it. Lower holes 237 will aid in the alignment of lower fixation screws 128 with the lower fixation holes 126, and upper holes 239 will aid in the alignment of upper fixation screws 114 with upper fixation holes 116.

Rod coupling bolt 260 comprises a rotatable shaft 262, with external threads 264 at upper end 266. Shaft 262 also has a knurled surface 263 (or a shaped flattened head, etc.) to allow the surgeon to firmly grip and rotate the shaft during the operation, so that the threaded tip can be tightened within, or loosened from, accommodating threads inside the shaft of a vertical rod. These threads are shown as threads 127 in FIG. 3.

Shaft 262 rotates within sleeve 268. A set of alignment fins 270 are provided at the upper end (the "shoulder") of sleeve 268. These alignment fins 270 are positioned in a "cruciate" configuration (i.e., in a shape resembling a cross, with four fins spaced equidistant from each other around the center axis of the sleeve; this can also be called an "orthogonal" arrangement, since each fin is aligned perpendicular to the two fins flanking it, around the center axis). These alignment fins interact with a set of accommodating slots 129 which are positioned around the circular rim of the base 124 of rod 110.

The sleeve 268 of bolt 260 can be held in a secure and non-rotating manner in the jig base 232 using any suitable means, such as a collar device 280. This collar device (or the external surface of the base of sleeve 268, if such a collar is not used) can be provided with any suitable means to prevent rotation of the sleeve within jig base 232, such as an additional set of alignment fins, or any other non-circular shape. Alternately, the lower tip of collar 280 can be externally threaded, so that the collar can be securely locked in place using a threaded nut (not shown in FIG. 6) positioned on the underside of jig base 232.

During the surgical insertion of rod 110, the rod is mounted securely (in a fixed and non-rotating manner) to the jig bolt 260, in a position which aligns the two upper jig holes 239 with the two upper rod holes 116. In a preferred method of insertion, the jig is positioned so that it will be on the medial (inside) position of the patient's foot during insertion of the rod. Accordingly, once the rod has been inserted to its desired final depth, upper jig holes 239 provide alignment guides that will allow the surgeon to drill two "transverse" holes through the tibia. Each hole will pass all the way through (i) the medial surface of the tibial bone, (ii) one of the upper rod holes 116, and (iii) the lateral surface of the tibial bone. The drill bit is then withdrawn, and a fixation screw is then driven or screwed into the bone and through a rod hole 116.

When both upper fixation screws have been securely inserted, the inner shaft 262 of the jig bolt 260 is rotated, using the knurled end 263, in a manner which loosens the threaded bolt tip end 266 from the accommodating threads inside rod. When the threaded shaft 262 has been loosened a sufficient amount to disengage the alignment fins 270 from the accommodating slots inside the shaft of rod 110, the jig can be rotated in increments of 90 degrees, so that the alignment fins 270 will reengage the accommodating slots inside the shaft of rod 110. This will position the oblique arm 234 and vertical arm 236 on the posterior surface of the patient's heel, and it will cause the hole 235 in oblique arm 234 to be aligned with the oblique hole 119 which passes through vertical rod 110. This allows jig hole 235 to serve as an alignment guide, as an oblique hole is drilled into the patient's calcaneal bone and then into the lower end of the patient's tibial bone. During this drilling operation, substantial pressure preferably should be placed on the horizontal base 232 of jig 230, to press the calcaneal bone firmly against the lower end of the tibial bone. Compression of the two bones against each other during the drilling step will help align the holes in the calcaneal and tibial bones properly, so that the oblique screw will maintain stable and secure compression between the two bones after the surgery has been completed.

After the oblique hole has been drilled and the oblique screw has been set and secured, the inner shaft 262 of bolt 260 is loosened once again, the alignment fins 270 are disengaged from the accommodating slots inside rod 110, and the jig is rotated 90 degrees again, so that the oblique and vertical arms are positioned on the lateral (outside) position of the patient's foot. The shaft 262 is then tightened, and the two lower holes 237 in jig arm 236 are used by the surgeon as alignment guides while he drills two transverse holes into the calcaneal bone. These two holes will be aligned with the two calcaneal (lower) fixation holes 126 in vertical rod 110. After the holes have-been drilled, the two calcaneal fixation screws 128 are inserted. This completes the placement and fixation of the rod and screw. The surgeon then does any necessary additional and/or final work, confirms proper placement of all implants (using X-rays, etc.), and finally closes the incisions, to complete the operation.

Thus, there has been shown and described a new and useful type of surgical implant that can be used for various types of ankle arthrodesis. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Albee, F. H., *Bone Graft Surgery*, p. 335 (W. B. Saunders, Philadelphia, Pa., 1915)

Albert, G., Kinige Falle von kunstlicher Anklosen bildung an paralytischen Gleidmassen (Weiner Medizinische Press, 1882)

Lexer, E., "Die verwegund der freien knochenplastik nebst versuchen uber gelenkversteifung und gelenktransplanten," Langenbecks Archive fur Klin Chirung 86: 9–38 (1906)

Pappa, J. A., et al, "Pantalar and tibiotalocalcaneal arthrodesis for post-traumatic osteoarthrosis of the ankle and hindfoot," *J Bone Joint Surg.* 74A: 1012–1019 (1992)

Quill, G. E., Jr, "The use of a second-generation intramedullary nail in the fixation of difficult ankle and hindfoot arthrodeses," *Amer. J. Orthopedics, Suppl.* 28(1S): 23–31 (1999)

Russotti, G. M., et al, "Tibiotalocalcaneal arthrodesis for arthritis and deformity of the hind part of the foot," *J Bone Joint Surg.* 70A: 1304–1307 (1988)

What is claimed is:

1. A surgical implant kit designed for ankle arthrodesis, comprising:

a. at least one tibio-calcaneal rod having a tip, a shaft, and a base, said rod being properly sized and suited for surgical insertion through a calcaneal bone so that the tip enters a tibial bone to establish tibio-calcaneal arthrodesis, and having an oblique hole passing through the shaft to accommodate a screw; and, b. at least one screw having a base, a shaft, and a threaded tip region, said threaded tip region being small enough to pass through the oblique hole in the shaft of the tibio-calcaneal rod, and said screw being properly sized and suited for surgical insertion at an angle through a calcaneal bone in a manner which causes at least a portion of the threaded tip region to enter a lower end of a tibial bone, wherein the oblique hole passes through the shaft of the rod at an angle with respect to the shaft, and wherein the rod and screw are designed to fit together inside an ankle joint, thereby establishing an ankle arthrodesis assembly, and wherein the threaded tip region of the screw allows the screw to establish compression of the tibial bone against the calcaneal bone when the screw is rotated during a surgical emplacement procedure.

2. The surgical implant kit of claim 1, wherein said angle is within a range of about 30 to about 50 degrees, measured between the tip of the rod and the tip of the screw.

3. The surgical implant kit of claim 1, wherein the rod and screw are enclosed within a sealed package that maintains sterility of the rod and screw until the package is opened.

4. The surgical implant kit of claim 1, wherein the screw also has external threads in a region proximate to the base of the screw.

5. The surgical implant kit of claim 4, wherein the external threads that are proximal to the base of the screw have a different pitch than the threaded tip region of the screw.

6. A surgical implant device for ankle arthrodesis, comprising a screw having a base, a shaft, and a threaded tip region, said threaded tip region being properly sized and suited for surgical insertion through a calcaneal bone in a manner which causes at least a portion of the threaded tip region to (i) enter a lower end of a tibial bone, and (ii) establish compression of the tibial bone against the calcaneal bone when the screw is rotated during a surgical emplacement procedure, and wherein said screw is packaged in a manner suited for a surgical implant and labelled in a manner which indicates that it is a medical device intended for ankle arthrodesis.

7. The surgical implant device of claim 6, wherein the screw is enclosed within a sealed package that maintains sterility of the screw until the package is opened.

8. The surgical implant device of claim 6, wherein the screw also has external threads in a region proximate to the base of the screw.

9. The surgical implant device of claim 8, wherein the external threads that are proximal to the base of the screw have a different pitch than the threaded tip region of the screw.

10. A method of establishing ankle arthrodesis in a patient in need thereof, comprising the following steps:

a. inserting a tibio-calcaneal rod having a tip, a shaft with an oblique hole passing through it, and a base, into a calcaneal bone in a manner that causes the tip to enter a tibial bone;

b. inserting a screw having a base, a shaft, and a threaded tip region into a calcaneal bone and through the oblique hole in the tibio-calcaneal rod, in a manner which causes at least a portion of the threaded tip region to enter into and engage a lower end of a tibial bone; and, c. rotating the screw in a manner which causes the threaded tip region of the screw to pull the tibial bone toward the calcaneal bone, in a manner which compresses the tibial bone against the calcaneal bone.

11. An alignment jig for assisting with implantation of a vertical rod and an oblique screw during ankle arthrodesis surgery, comprising:

a. a jig base component which will be positioned adjacent to a bottom surface of a patient's heel during a surgical operation;

b. a jig arm component which will be positioned roughly parallel to a patient's tibia bone during a surgical operation, and which is provided with a plurality of fixation screw alignment holes to assist a surgeon in drilling holes to accommodate fixation screws that will enter fixation screw holes in the vertical rod; and, c. an oblique jig hole passing through the alignment jig, located in a position which will align with an oblique rod hole passing through the vertical rod when the vertical rod is coupled to the alignment jig in a position suited for drilling an oblique hole through the patient's heel; and, d. a rod coupling component which extends outwardly from the base component while the alignment jig is in use during a surgical operation, and which is provided with means for engaging the vertical rod in a manner which:

(i) allows controlled alignment of at least one fixation screw alignment hole in the jig arm with at least one fixation screw hole in the vertical rod, and prevents rotation of the rod relative to the alignment jig during a bone-drilling operation;

(ii) allows controlled rotation of the alignment jig with respect to the vertical rod after a first bone-drilling operation has been completed and before a second bone-drilling operation commences; and, (iii) allows controlled alignment of the oblique jig hole with the oblique rod hole passing through the vertical rod, and prevents rotation of the rod relative to the alignment jig while an oblique hole is being drilled for placement of the oblique screw.

12. The alignment jig of claim 11, wherein the oblique jig hole passes through an oblique arm component which couples the jig base component to the jig arm component.

13. The alignment jig of claim 11, wherein the rod coupling component comprises a threaded shaft which can be rotated within a sleeve component.

14. The alignment jig of claim 13, wherein the sleeve component is provided with alignment fins.

15. The alignment jig of claim 14, wherein four alignment fins are provided in a cruciate orientation.

* * * * *